（12) United States Patent
Park et al.

(10) Patent No.: US 7,416,880 B2
(45) Date of Patent: Aug. 26, 2008

(54) ***METARHIZIUM* GENUS MICROORGANISM AND THE METHOD FOR CONTROLLING THE SOIL PESTS USING THE SAME**

(75) Inventors: Ho Yong Park, Taejeon (KR); Kwang Hee Son, Taejeon (KR); Eun Young Suh, Kangwon-do (KR); Ki-Duk Kim, Taejeon (KR); Dong Ha Shin, Taejeon (KR)

(73) Assignee: Korea Research Institute of Bioscience and Biotechnology, Taejeon (KR)

( * ) Notice: Subject to any disclaimer, the term of this patent is extended or adjusted under 35 U.S.C. 154(b) by 0 days.

(21) Appl. No.: 10/494,111

(22) PCT Filed: Nov. 2, 2002

(86) PCT No.: PCT/KR02/02039

§ 371 (c)(1),
(2), (4) Date: Sep. 7, 2004

(87) PCT Pub. No.: WO03/038065

PCT Pub. Date: May 8, 2003

(65) Prior Publication Data

US 2005/0019309 A1    Jan. 27, 2005

(30) Foreign Application Priority Data

Nov. 2, 2001    (KR) .................... 10-2001-0068126

(51) Int. Cl.
*C12N 1/14*    (2006.01)
*A61L 101/52*    (2006.01)
*A01N 25/12*    (2006.01)
*A01N 25/14*    (2006.01)

(52) U.S. Cl. .................... 435/254.1; 435/267; 424/408; 424/409

(58) Field of Classification Search .............. 435/254.1, 435/267; 424/408, 409
See application file for complete search history.

(56) References Cited

U.S. PATENT DOCUMENTS 4,957,935 A * 9/1990 Inamori et al. .............. 514/383

(Continued)

FOREIGN PATENT DOCUMENTS

JP    H2-88510    3/1990

(Continued)

OTHER PUBLICATIONS

Clarkson et al., "New insights into the mechanisms of fungal pathogenesis in insects," Trends in Microbiology 4(5):197-203, 1996.*

(Continued)

*Primary Examiner*—Jon P Weber
*Assistant Examiner*—Rosanne Kosson
(74) *Attorney, Agent, or Firm*—Klarquist Sparkman, LLP

(57) ABSTRACT

The present invention relates to a novel fungus of *Metarhizium* genus and a method for controlling soil pests using the same, more particularly to a novel *Metarhizium anisopliae* HY-2 and a microbial insecticide comprising the same and a method for controlling soil pests using the same. The *Metarhizium anisopliae* HY-2 can effectively be used to control the soil pests such as Scarabaeidae.

11 Claims, 7 Drawing Sheets

U.S. PATENT DOCUMENTS 5,595,746 A 1/1997 Milner et al.
5,989,898 A 11/1999 Jin et al.
6,280,723 B2 * 8/2001 Stimac et al. .............. 424/93.5

FOREIGN PATENT DOCUMENTS

JP 2001-78751 A 3/2001

OTHER PUBLICATIONS

Hoog, Atlas of clinical fungi: 734, 2000, *Metarhizium anisopliae*, Sorokin strains, a record in the CBS fungi database for *Metarhizium anisopliae*, http://www.cbs.knaw.nl/databases / index.htm, printed on Mar. 7, 2006.*

Clarkson and Charnley, "New Insights Into the Mechanisms of Fungal Pathogenesis in Insects," *Trends in Microbiology* 4:197-203 (1996).

* cited by examiner

*METARHIZIUM* GENUS MICROORGANISM AND THE METHOD FOR CONTROLLING THE SOIL PESTS USING THE SAME

This is the U.S. National Stage of International Application No. PCT/KR02/02039, filed Nov. 2, 2002 (published in English under PCT Article 21(2)), which in turn claims the benefit of Korean patent application no. 2001/68126, filed Nov. 2, 2001.

FIELD OF THE INVENTION

The present invention relates to a novel fungus of *Metarhizium* genus and a method for controlling soil pests using the same, more particularly to a novel *Metarhizium anisopliae* HY-2 and a microbial insecticide comprising the same and a method for controlling soil pests using the same.

BACKGROUND ART OF THE INVENTION

Pests cause a great loss to major agricultural products and various useful plants every year. To control the pests, 1,205 kg/km$^2$/year of agricultural chemicals (pesticides) have been used in Korea since mid 1990s, which is 4.6 fold much as average amount (263 kg) used in OECD countries and 48 times much as a minimum 25 kg used in New Zealand. Mostly organic pesticides and chemical insecticides have been used, resulting in the destruction of ecosystem, underground water-contamination, increased toxicity remaining in agricultural products and the appearance of pests having strong resistance. Countries brought about an agreement to reduce organic pesticide quantity used every year about 50% until 2004 at Rio environmental conference held in 1992. In fact, 46% of conventional organic insecticides, especially 68% in vegetables and fruits growing fields, were substituted with alternative pesticides in the United States in 1997, in order to control pests with less damage to environment.

A pest controlling method using insect pathogenic microorganism is an environmental protective control means that works selectively for target pests only, prohibits the appearance of pests having resistance, is available lastingly and makes possible to produce agricultural products in good quality without residual toxicity and without harming human, animals, plants and environment. Thus, many advanced countries in the field of agriculture including US have been separated insect pathogenic microorganisms suitable for their own countries' condition, mass-produced and put to use thereof actually.

Though the environmental protective biotic pesticide takes just about 5% of total pesticide market, it grows as fast as more than 20% every year owing to the recognition of importance of biotic pesticide. So, biotic pesticides are expected to take huge part of the market in years. When domestic market is open for alternative pesticides, it will be taken over by countries that have already developed biotic pesticides using insect pathogenic microorganisms since Korea has depended on only organic pesticides. Then, Korea's foreign exchange holdings will be decreased and export of domestic agricultural products produced by chemical pesticides will be obstructed. In order to cope with such difficult situation effectively, it is urgently required to develop biotic (microbial) pesticides using insect pathogenic microorganisms suitable for our agricultural environment.

As a kind of soil pests, *Mimela splendens* (gold bug) is a euryphagous pest harming plants, especially plants of Rosaceae, Salicaceae, Fagaceae, Betulaceae and Aceraceae. Some adults of soil pests harm leaves of crops or plants and larvae do roots of various crops and grass. The gold bugs damage not only various broad-leaved trees in forest but general crops like corns or tomatoes, fruits like apples or apricots, flowers like chrysanthemums or roses, tea plants, many herbs, ginseng farms, etc (Lee et al, Korean Journal of Applied Entomology, 1997, 36, 2, 156-165).

The larvae of gold bugs developing and living in golf courses directly harm grass roots to death and indirectly provide themselves as feed for birds, causing digging up the grass. Therefore, they have a bad effect on the preservation of grass quality (Chu et al, Korean Journal of Turfgrass Science, 1998, 12, 3, 225-236; Lee et al, Korean Journal of Applied Entomology, 1997, 36, 2, 156-165; Lee, PhD Thesis, 2000). To control such soil insects like gold bugs, fenitrothion emulsion, chlorpyrifos-methyl emulsion and ethoprophos granules have been used. But those chemical pesticides have effects on only just-hatched larvae (the first larva stage). Thus, catching the right time is essential for controlling those insects. By the way, those chemical pesticides weaken the grass and cause overdose (Korea Patent Application #1999-15472).

Great efforts have been made to control soil pests like gold bugs, *Encarcia formosa*, *Eretmocerus eremicus*, *Plutella xylostella*, *Spodoptera litura* and *Nilaparvata lugens*. But using the conventional chemical pesticides causes not only high expense but also such problems that the destruction of ecosystem, the under water contamination, the residual toxicity in agricultural products and the appearance of insects having resistance.

Thus, in order to develop an environmental protective controlling method, the present inventors have searched insect pathogenic microorganisms that are good for controlling soil pests especially harming major agricultural products and confirmed that a fungus of *Metarhizium* genus kills soil pests including the larvae of gold bugs. So, the present inventors have completed the present invention by preparing a microbial insecticide comprising the fungus of *Metarhizium* genus for controlling soil pests.

SUMMARY OF THE INVENTION

The present invention relates to a novel fungus of *Metarhizium* genus and a method for controlling soil pests using the same, more particularly to a novel *Metarhizium anisopliae* HY-2 and a microbial insecticide comprising the same and a method for controlling soil pests using the same. The *Metarhizium anisopliae* HY-2 can effectively be used to control the soil pests such as Scarabaeidae.

DETAILED DESCRIPTION OF THE INVENTION

To achieve the above object, the present invention provides a novel fungus of *Metarhizium* genus that is useful for controlling soil pests harming major crops.

The present invention also provides a medium for mass-production of a fungus of *Metarhizium* genus.

The present invention further provides a microbial insecticide comprising the above fungus of *Metarhizium* genus for controlling soil pests and a preparation method thereof.

Further features of the present invention will appear hereinafter.

The present invention provides a novel microorganism *Metarhizium anisopliae* HY-2 having specific insectisidal effect on soil pests.

Figure 1:
FIG. 1 is an electron microphotograph showing the *Metarhizium anisopliae* HY-2 of the present invention.

The present inventors separated a microorganism having insecticidal effect on soil pests from dead insects infected with insect pathogenic microorganisms and soil samples where soil pests were inhabited. The microorganism of the present invention was identified as a kind of *Metarhizium anisopliae* (see FIG. 1). The microorganism of the present invention was named as "*Metarhizium anisopliae* HY-2" and deposited at Gene Bank of Korea Research Institute of Bioscience and Biotehnology on Mar. 10, 1995 (Accession No: KCTC 0156BP).

The present invention also provides a medium for economical mass-production of the above fungus of *Metarhizium* genus.

The medium of the present invention was prepared by mixing carbon source, nitrogen source and inorganic elements with water. Autoclave is preferred for the preparation of the media.

As for a carbon source, glucose, cornstarch, saccharose, molasses, wheat bran, rice bran, etc were preferably used and wheat bran or rice bran was more preferred. As for a nitrogen source, yeast extract, soybean flour, corn-immersion, malt extract, peptone, etc were preferably used and yeast extract was more preferred. As for an inorganic element, potassium chloride (KCl), magnesium sulfonate ($MgSO_4$), ferroic sulfate ($FeSO_4$), sodium nitrate ($NaNO_3$), dipotassium phosphate ($K_2HPO_4$), etc were preferably used and sodium nitrate was more preferred.

The present invention further provides a microbial insecticide comprising a fungus of *Metarhizium* genus for controlling soil pests and a preparation method thereof.

Microbial insecticides of the present invention containing a fungus of *Metarhizium* genus for controlling soil pests can be prepared in the form of either wettable powders or tablets.

The wettable powders of the above microbial insecticides can be obtained by pulverization after drying solid media inoculated with *Metarhizium anisopliae* HY-2 and mixing surfactant and diluent with it.

Surfactants used for preparing wettable powders of the above microbial insecticides can be selected from a group consisting of poly carboxylate, sodium lingo sulfate, sodium dialkyl sulfosuccinate, sodium alkyl sulfonate, polyoxy ethylene alkyl phenyl ether, sodium tripolyphosphate, polyoxyethylene alkyl aryl phosphoric ester, polyoxyethylene alkyl aryl ether, polyoxyethylene alkyl arylpolymer, polyoxyalkylon alkyl phenyl ether, polyoxyethylene nonyl phenyl ether, sodium sulfonate, naphthalene formaldehyde, triton 100 and tween 80. Diluents can be selected from a group consisting of soybean flour, rice, wheat, yellow earth and diatomaceous earth.

The granules of the above microbial insecticides contain spores of *Metarhizium anisopliae* HY-2, surfactants, nutrients and disintegrators, and can include diluents additionally.

The tablets of microbial insecticides of the present invention are preferably prepared with the following weight ratios: *Metarhizium anisopliae* HY-2 spores 10-60 weight parts, surfactants 2-16 weight parts, nutrients 5-20 weight parts, disintegrators 10-30 weight parts. Inactive carriers, preservatives, wetting agents, supply accelerants, attractants, encapsulating agents, binders, emulsifiers, dyes, UV protectors, buffers, fluids, etc can be additionally added for the preparation of the tablets of microbial insecticides of the present invention.

Surfactants used for preparing tablets of the above microbial insecticides can be selected from a group consisting of poly carboxylate, sodium lingosulfate, sodium dialkyl sulfosuccinate, sodium alkyl sulfonate, polyoxyethylene alkyl phenyl ether, sodium tripolyphosphate, polyoxyethylene alkyl aryl phosphoric ester, polyoxyethylene alkyl aryl ether, polyoxyethylene alkyl arylpolymer, polyoxyalkylon alkyl phenyl ether, polyoxyethylene nonyl phenyl ether, sodium sulfonate and naphthalene formaldehyde.

Nutrients can be selected from a group consisting of dextrin, glucose and starch, disintegrators can be selected from a group consisting of bentonite, talc, dialite, kaolin and sodium carbonate, and diluents can be selected from a group consisting of lignin, lignin sulfate and eatomaceus ether.

Figure 2:
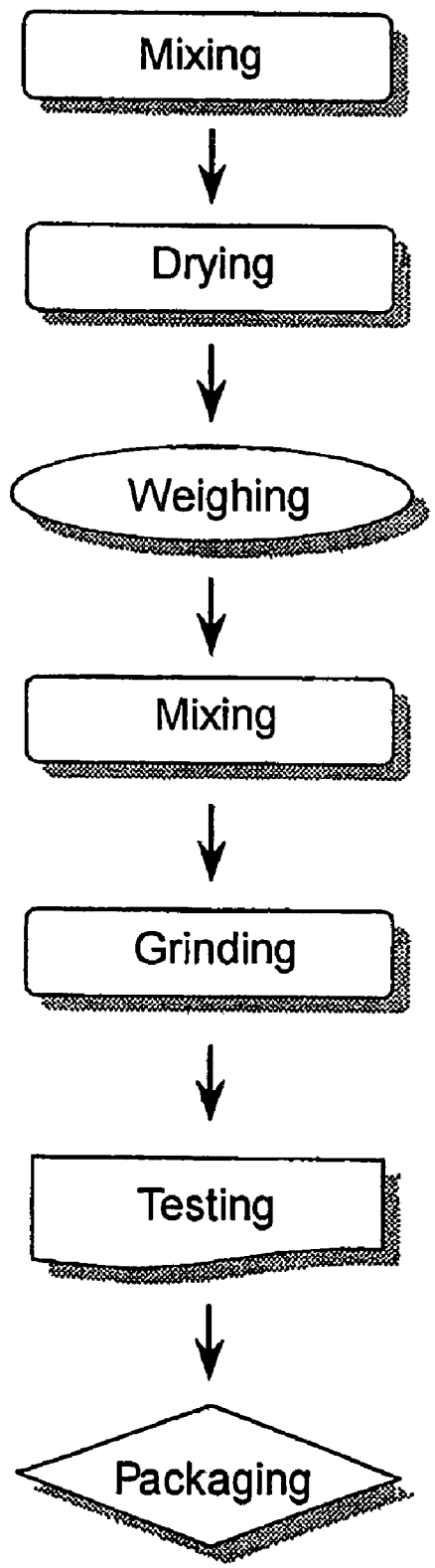
FIG. 2 is a diagram showing the manufacturing process of a microbial insecticide hydrate comprising the *Metarhizium anisopliae* HY-2 of the present invention for controlling soil pests.

The preparation method for wettable powders of microbial insecticides of the present invention comprises the following steps:

1) Pulverizing after drying solid media inoculated with *Metarhizium anisopliae* HY-2; and 2) Adding surfactants and diluents to the pulverized powders of the above step 1) and then pulverizing thereof again (see FIG. 2).

Figure 3:
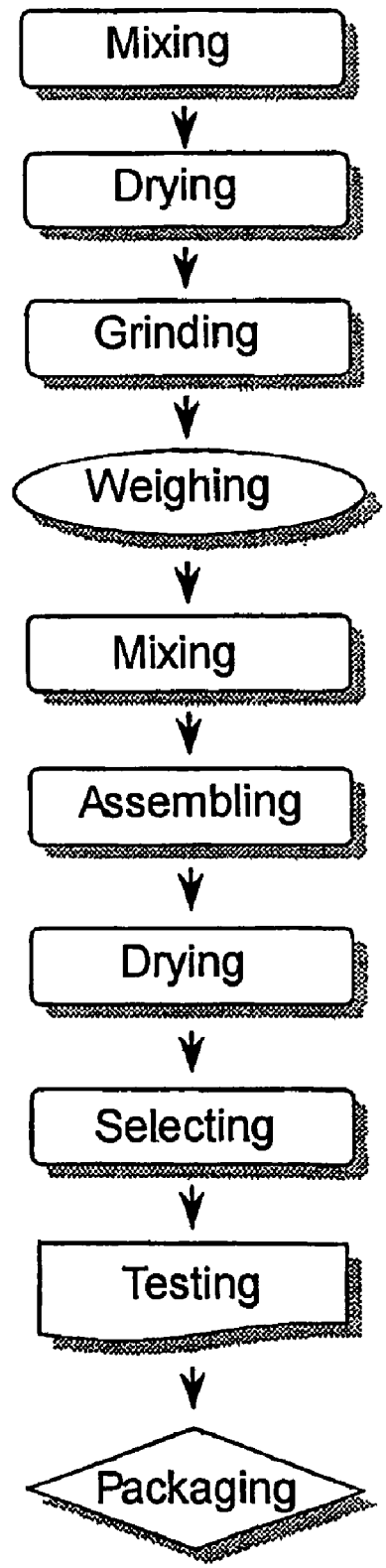
FIG. 3 is a diagram showing the manufacturing process of a microbial insecticide granule comprising the *Metarhizium anisopliae* HY-2 of the present invention for controlling soil pests.

And, the preparation method for granules of microbial insecticides of the present invention comprises the following steps:

1) Pulverizing after drying solid media inoculated with *Metarhizium anisopliae* HY-2;

2) Adding surfactants, adjuvant and diluents to the pulverized powders of the above step 1) and then kneading thereof with water; and 3) Granulating the dough prepared in the above step 2) and then drying thereof (see FIG. 3).

The present inventors tested if the medium of the present invention was suitable for mass-production of *Metarhizium anisopliae* HY-2. As a result, $10^8$ cells were obtained in the second week of culture and even though early growth rate of bacteria depended on the amount of inoculum, the bacteria were kept growing well regardless of the amount of inoculum as culture continued, suggesting that the medium of the present invention was suitable for mass-production of the bacteria (see FIG. 4).

The present inventors also investigated the insecticidal effect of *Metarhizium anisopliae* HY-2 of the present invention on gold bugs using dipping method. As a result, spore-suspension solution of *Metarhizium anisopliae* HY-2 was confirmed to have excellent insecticidal effect (56-64%) while a control group showed just 13-26% insecticidal effect (see FIG. 5). In addition, the larvae of *Adoretus tenuimaculatus* infected with *Metarhizium anisopliae* HY-2 were detected after a while (see FIG. 6).

The present inventors further confirmed the insecticidal effect of *Metarhizium anisopliae* HY-2 of the present invention on gold bugs using contact toxicity test. As a result, *Metarhizium anisopliae* HY-2 was confirmed to have excellent insecticidal effect (60-64%) while a control group showed just 20-27% insecticidal effect (see FIG. 7).

Therefore, the *Metarhizium anisopliae* HY-2 of the present invention was proved to have excellent insecticidal effect on soil pests.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Separation and Identification of Microorganisms

In order to separate microorganisms that are useful for controlling soil pests, the present inventors collected dead insects infected with insect pathogenic microorganisms and at the same time, picked insects from soil samples where soil pests were inhibiting as well. Particularly, the present inventors crushed soil pests dead by infection with insect pathogenic microorganisms and diluted with sterile water. Took 0.1 ml of suspension and smeared on microorganism test medium (Dermatophyte test medium) as presented in Table 1. Suspended 0.1 g of soil samples with 5 ml of sterile water and smeared on microorganism test medium as well. Culture thereof at 30° C. for 5 days and made a selection, which was inoculated on new DTM medium and further cultured under the same condition above.

TABLE 1

| Ingredient | Amount (%) |
|---|---|
| Glucose | 2 |
| Soytone | 1 |
| Phenol Red | 0.02 |
| Cycloheximide | 0.05 |
| Chloheximide | 0.01 |
| Gentamycine | 0.01 |
| Agar | 1.5 |
| Acetone (w/w) | 2 |

As a result, the present inventors separated microorganism showed excellent controlling effect on soil pests, and identified thereof. The microorganism was identified as a kind of *Metarhizium anisopliae* (FIG. 1), named as "*Metarhizium anisopliae* HY-2" and deposited at Gene Bank of Korea Research Institute of Biosciene and Biotehnology on Mar. 10, 1995 (Accession No: KCTC 0156BP).

Example 2

Preservation and Cultivation of the Separated Microorganism

For the pre-culture of *Metarhizium anisopliae* HY-2 of the present invention separated in the above Example 1 for further mass-culture and preservation, CDAY medium prepared by adding yeast extract to Czapek medium (Czapek-Dox broth, DIFCO) was used (Table 2).

TABLE 2

| Ingredient | Amount (%) |
|---|---|
| Bacto saccharose | 3 |
| Sodium nitrate | 0.3 |
| Diphotassium phosphate | 0.1 |
| Mangnessium sulfate | 0.05 |
| Potassium chloride | 0.05 |
| Ferrious sulfate | 0.001 |
| Yeast extract | 0.5 |

CDAY plate medium containing 2% agar was used for the preservation of microorganisms, which was cultured at 26° C. for about 15 days until spores were formed. Cut the medium on which hyphae of microorganisms were blooming by sterilized stick-like test spoon with making blocks. Set the test spoon straight, so that three dimension on medium were touched by that. Untouched one side was taken and preserved in a container containing distilled water including 15% glycerol at −70° C.

CDAY medium was autoclaved at 121° C. for 20 minutes, after which bacteria were inoculated thereto and shaking-cultured at 26° C. with 180 rpm for 4-5 days.

Example 3

Preparation of Medium for Mass-production

The present inventors prepared a commercial medium for mass-production of a fungus of *Metarhizium* genus of the present invention. Particularly, mixed 3 l of water, 4 kg of wheat bran and 2 kg of rice bran together in an automatic mixer for 6 minutes. Put the mixture in a polypropylene bag (50×22×10 cm$^2$) for autoclave to which 2 sheets of filter membrane (7×7 cm$^2$, effective area diameter 3.5 cm) were attached for air-permeability. After sealing the bag, performed autoclave at 121° C. for 30 minutes, resulting in the preparation of a commercial culture medium for mass-production.

Example 4

Preparation of Wettable Powders of Microbial Insecticide

The present inventors prepared wettable powders (WP) that can be easily hydrated as being diluted with water in order to provide *Metarhizium anisopliae* HY-2 raw-powders stably. Particularly, heated the solid medium prepared in Example 3 that was inoculated with *Metarhizium anisopliae* HY-2 in a dry oven at 70° C. for 2 hours. Upon finishing drying, pulverized thereof. Add 10% surfactants and 40-60% diluents to the above 30-50% raw-powders and mixed well. Pulverized the mixture with a grinder (Jet-O-mill, Aljet) and then tested hydrating capacity for the preparation of wettable powders (FIG. 2).

In order to confirm the stability of the microbial insecticides for controlling soil pests prepared above, performed preservation test on the wettable powders of the present invention. As a result, the microbial insecticides showed about 45% recovery rate ($4.19 \times 10^8$ spores/g).

Example 5

Preparation of Microbial Insecticide Granules

The present inventors prepared granules (GR) that could be used as they were in order to provide *Metarhizium anisopliae* HY-2 raw-powders stably. Particularly, heated the solid medium inoculated with *Metarhizium anisopliae* HY-2 in a dry oven at 70° C. for 2 hours. After finishing drying, pulverized thereof. Add 3% surfactants, 2% adjuvants and 10-30% diluents to the above 30-50% raw-powders and then mixed well. Kneaded the mixture with 35% water. Upon finishing kneading, granulated thereof (diameter: 1 mm, length: 1-5 mm) using Basket type extruder (Fuji powder Co) and then dried in a dry oven at 70° C. Removed dusts by sieving the dried materials with a 16-30 mesh sieve, resulting in the preparation of microbial insecticide granules (FIG. 3).

In order to confirm the stability of the microbial insecticides for controlling soil pests prepared above, performed preservation test on the granules of the present invention. As a result, the microbial insecticides showed about 30% recovery rate ($7.14 \times 10^6$ spores/g).

<5-1> Preparation of Microbial Insecticide Granules 1

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 15% sodium tripolyphosphate (Hannong chemicals Inc.), 15% polycarboxylate (Hannong chemicals Inc.) and 20% talc (Table 3).

TABLE 3

| Granules | Effective Ingredient | | Surfactants | | Nutrients | | Disintegrators | |
|---|---|---|---|---|---|---|---|---|
| 1 (Example 5-1) | Spores of HY-2 | 50% | Sodiumtripolyphosphate Polycarboxylate | 15% 15% | | | Talc | 20% |
| 2 (Example 5-2) | Spores of HY-2 | 50% | Polycarboxylate Sodiumlignosulfonate Sodium dialkyl sulfosuccinate | 3% 3% 1% | Glucose | 10% | Bentonite Calciumcarbonate | 20% 13% |
| 3 (Example 5-3) | Spores of HY-2 | 50% | Sodium alkyl aryl sulfonate Polyoxyethylene alkyl phenylether Sodium dialkyl sulfosuccinate | 5% 1% 1% | Starch | 10% | Talc | 30% |
| 4 (Example 5-4) | Spores of HY-2 | 50% | Polycarboxylate Polyoxyethylene alkyl phenyl ether Calciumlignosulfonate | 3% 1% 3% | Starch | 10% | Bentonite Talc | 20% 13% |
| 5 (Example 5-5) | Spores of HY-2 | 50% | Polyoxyethylene alkyl aryl phosphoric ester Polyoxyethylene alkyl aryl ether and polyoxyethylene alkyl aryl polymer | 5% 3% | Glucose | 10% | Bentonite Talc | 20% 12% |
| 6 (Example 5-6) | Spores of HY-2 | 50% | Polyoxyethylene alkyl phenyl ether Sodiumtripolyphosphate | 1% 3% | Staech | 10% | Bentonite Talc | 20% 16% |
| 7 (Example 5-7) | Spores of HY-2 | 50% | Polycarboxylate Polyoxyethylene alkyl aryl ether and polyoxyethylene alkyl aryl polymer | 3% 5% | Starch | 10% | Bentonite Kaolin | 20% 12% |
| 8 (Example 5-8) | Spores of HY-2 | 50% | Polycarboxylate Sodium alkyl aryl sulfonate Sodium dialkyl sulfosuccinate | 3% 5% 1% | Starch | 10% | Dialite Calciumcarbonate | 20% 11% |
| 9 (Example 5-9) | Spores of HY-2 | 50% | Sodiumtripolyphosphate Polyoxyethylene alkyl aryl phosphoric ester | 3% 5% | Starch Dextran | 10% 10% | Bentonite Dialite | 10% 12% |

TABLE 3-continued

| Granules | Effective Ingredient | | Surfactants | | Nutrients | | Disintegrators | |
|---|---|---|---|---|---|---|---|---|
| 10 (Example 5-10) | Spores of HY-2 | 50% | Polyoxyethylene alkyl aryl polymer special | 5% | Dextran | 5% | Bentonite Talc | 20% 12% |
| | | | Calciumlignosulfonate | 5% | | | | |
| | | | Polycarboxylate | 3% | | | | |
| 11 (Example 5-11) | Spores of HY-2 | 50% | Polyoxyalkylon alkyl phenyl ether | 3% | Dextran Staech | 5% 10% | Calciumcarbonate | 28% |
| | | | Sodiumtripolyphosphate | 3% | | | | |
| | | | Sodium dialkyl sulfosuccinate | 1% | | | | |
| 12 (Example 5-12) | Spores of HY-2 | 50% | Sodiumlignosulfonate | 3% | Glucose | 10% | Kaolin Talc | 20% 14% |
| | | | Polyoxyethylene alkyl aryl ether polymer | 3% | | | | |
| 13 (Example 5-13) | Spores of HY-2 | 50% | Polyoxyethylene nonyl phenyl ether | 3% | Dextran | 5% | Kaolin Dialite | 20% 19% |
| | | | Sodium sulfonate naphthalene formaldehyde | 2% | | | | |
| | | | Sodium dialkyl sulfosuccinate | 1% | | | | |

<5-2> Preparation of Microbial Insecticide Granules 2

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% polycarboxylate, 1% sodium lignosulfonate, 10% glucose, 20% bentonite and 13% calcium carbonate (Table 3).

<5-3> Preparation of Microbial Insecticide Granules 3

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 5% sodium alkyl aryl sulfonate, 1% polyoxyethylene alkyl phenyl ether, 10% starch, 30% talc and 3% dialite (Table 3).

<5-4> Preparation of Microbial Insecticide Granules 4

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% polycarboxylate, 1% polyoxyethylene alkyl phenyl ether, 3% calcium lignosulfonate, 10% starch, 20% bentonite and 13% talc (Table 3).

<5-5> Preparation of Microbial Insecticide Granules 5

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 5% polyoxyethylene aryl phosphoric ester, 3% polyoxyethylene alkyl aryl ether and polyoxyethylene alkyl aryl polymer, 10% glucose, 20% bentonite and 12% talc (Table 3).

<5-6> Preparation of Microbial Insecticide Granules 6

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 1% polyoxyethylene alkyl phenyl ether, 3% sodium tripolyphosphate, 10% starch, 20% bentonite and 16% talc (Table 3).

<5-7> Preparation of Microbial Insecticide Granules 7

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% polycarboxylate, 5% polyoxyethylene alkyl aryl ether and polyoxyethylene alkyl aryl polymer, 10% starch, 20% bentonite and 12% kaolin (Table 3).

<5-8> Preparation of Microbial Insecticide Granules 8

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% polycarboxylate, 5% sodium alkyl aryl sulfonate, 1% sodium dialkyl sulfosuccinate, 10% starch, 20% dialite and 11% calcium carbonate (Table 3).

<5-9> Preparation of Microbial Insecticide Granules 9

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% sodiumtripolyphosphate, 5% polyoxyethylene alkyl aryl phosphoric ester, 10% starch, 10% dextrin, 10% bentonite and 12% dialite (Table 3).

<5-10> Preparation of Microbial Insecticide Granules 10

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 5% polyoxyethylene alkyl aryl polymer special, 5% calcium lignosulfonate, 3% polycarboxylate, 5% dextrin, 20% bentonite and 12% talc (Table 3).

<5-11> Preparation of Microbial Insecticide Granules 11

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% polyoxyalkylone alkyl phenyl ether, 3% sodium tripolyphosphate, 1% sodium dialkyl sulfosuccinate, 5% dextrin, 10% starch and 28% calcium carbonate (Table 3).

<5-12> Preparation of Microbial Insecticide Granules 12

The present inventors prepared granules having the same effect as the microbial insecticide granules for controlling soil pests prepared in the above Example 5. Precisely, the present inventors prepared microbial insecticides granules for controlling soil pests consisting of 50% *Metarhizium anisopliae* HY-2 spores, 3% sodium lignosulfonate, 3% polyoxyethylene alkyl aryl ether polymer, 10% glucose, 20% kaolin and 11% talc (Table 3).

<5-13> Preparation of Microbial Insecticide Granules 13

The present inventors prepared granules having the same effect as the microbial insecticide granules is for controlling soil pests prepared in the above Example 5. Precisely, the present inventors prepared microbial insecticides granules for controlling soil pests consisting of 50% *Metarhizium anisopliae* HY-2 spores, 3% polyoxyethylene nonyl phenyl ether, 2% sodium sulfonate naphthalene formaldehyde, 1% sodium dialkyl sulfosuccinate, 5% dextran, 5% kaolin and 1% dialite (Table 3).

Example 6

Preparation of Formulations for Capsulation of Microbial Insecticide

The present inventors prepared formulations for capsulation of microbial insecticide having the same effect as the microbial insecticide granules for controlling soil pests prepared in the above Example 5. Particularly, mixed 11% soybean flour, 6% mung beans, 4% rice flour, 4% potato starch, 4% rye flour and 3% yellow earth together and autoclaved thereof at 121° C. for 20 minutes. Before completely cooling down, mixed thereof well again and then cool it down in cold water. Mixed thoroughly over 1 minute using a stirrer (d=5 cm, over 200 rpm). While keeping on stirring, added additives and *Metarhizium anisopliae* HY-2 spores and mixed well again, resulting in the preparation of formulations for capsulation of microbial insecticide for controlling soil pests.

Example 7

Security of Test Insect

The present inventors used *Adoretus tenuinaculatus* among gold bugs, a kind of soil pests, as a test insect. The imagoes (adult insects) were collected in Yusung country club, Taejeon, Korea and bred through generations using a chestnut tree as a host plant. Tests were done within 2-4 generations. The larvae were bred with artificial feeds (sawdust:bed soil:water=5:3:2). Both imagoes and larvae of the test insects were bred in cages (30 cm×30 cm×50 cm) in which temperature was maintained at 25±2° C. and relative humidity was kept 60-70%.

Experimental Example 1

Mass-culture of a Fungus of *Metarhizium* Genus

The present inventors confirmed if the medium prepared in the above Example 3 was suitable for mass-production of *Metarhizium anisopliae* HY-2 of the present invention. Particularly, after liquid culturing *Metarhizium anisopliae* HY-2 that was stored at −70° C. in wheat bran medium (wheat bran 333 g, rice bran 167 g, $1^{st}$ distilled water 250 ml), inoculated thereof on the medium for mass-production prepared in Example 3 for further culture. Inoculated 2 ml ($7.76 \times 10^3$ cfu/g) and 10 ml ($3.38 \times 10^4$ cfu/g) of pre-cultured solution onto the 750 g of medium for mass-production of the present invention respectively, and then cultured them in a culture room for 3-4 weeks in which the temperature was maintained at 27° C., the radiation intensity was kept 40 W×2×1.5 and the relative humidity was kept 40-70%. Every 7 days after inoculation, the number of live bacteria was counted, so that the growth of *Metarhizium anisopliae* HY-2 according to the amount of inoculum could be observed. Specific growth rate ($\mu$ max) was measured based on the increased density of live bacteria. To calculate the specific growth rate, subtracted early density of live bacteria from late density of live bacteria, which was converted by log value and then subtracted beginning time from after-growth time therefrom, suggesting the growth rate of the number of live bacteria per hour.

Figure 4:
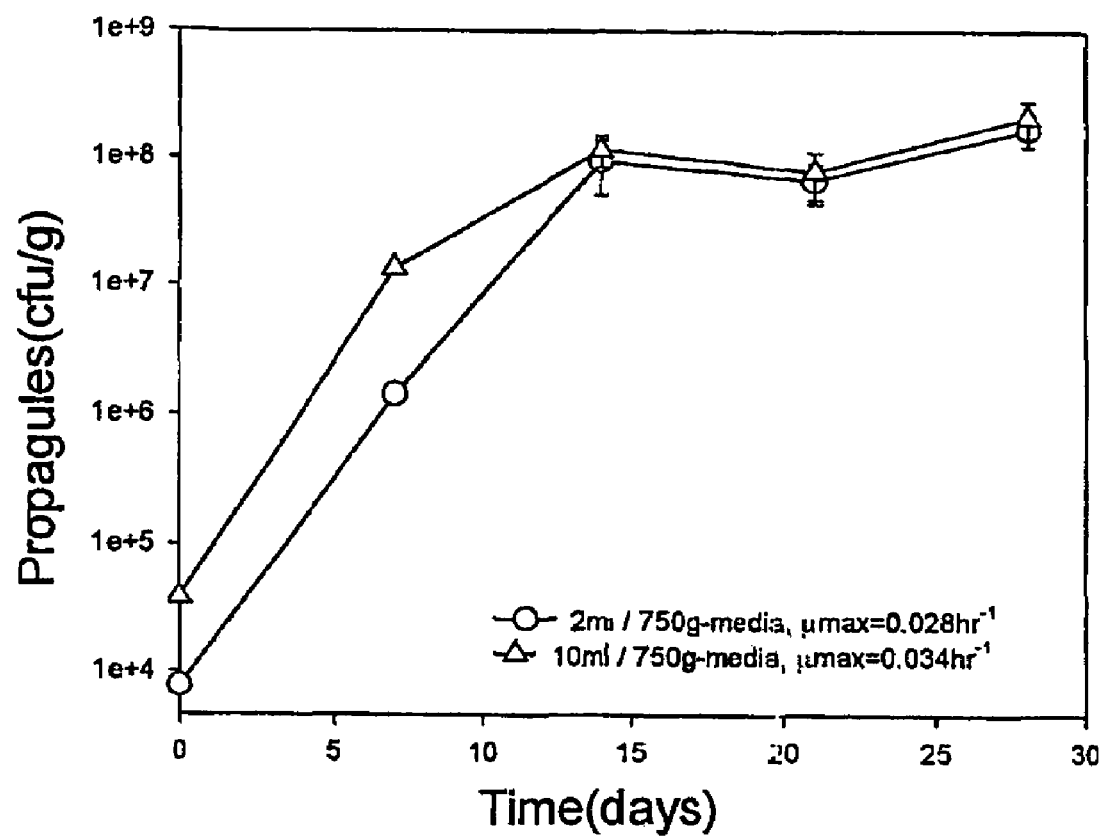
FIG. 4 is a graph showing the growth curve of the *Metarhizium anisopliae* HY-2 of the present invention.

As a result, when inoculated 2 ml of inoculum at the early stage, the growth speed for the early 2 weeks was 0.028 $hr^{-1}$ and when inoculated 10 ml of inoculum, the growth speed for the early weeks was 0.034 $hr^{-1}$. And the present inventors confirmed the efficiency of the medium for mass-production of the present invention by obtaining $10^8$ live bacteria on the second week of culture. Also, the present inventors confirmed that the early growth rate was depended on the amount of inoculum but the gap became smaller as culture progressed (FIG. 4).

Experimental Example 2

Confirmation of the Insecticidal Effect by the Dipping Method

The present inventors confirmed the insecticidal effect of *Metarhizium anisopliae* HY-2 of the present invention on gold bugs by dipping method. Particularly, shaking cultured *Metarhizium anisopliae* HY-2 on CDAY medium for 4 days (26° C., 180 rpm). Measured the density of spores with hemacytometer and adjusted the density to $1 \times 10^8$ 포자/ml using distilled water containing 0.05% tween-80. After dipping 10 larvae each from $1^{st}$ instar, $2^{nd}$ instar and $3^{rd}$ instar of *Adoretus tenuinaculatus* in spore suspension for 10 seconds, transferred them to artificial feeds (sawdust:bed soil:water=5:3:2) and raised them at 26-28° C. in dark condition. While keeping required humidity for 15 days, investigated pathogenesis. At that time, regarded insects on which hyphae of fungus were generated as dead insects and insects grown to next instar as live insects. Counted both numbers and presented them with percentage. All experiments were performed 5 times. Used distilled water containing 0.05% tween-80 for a control group.

Figure 5:
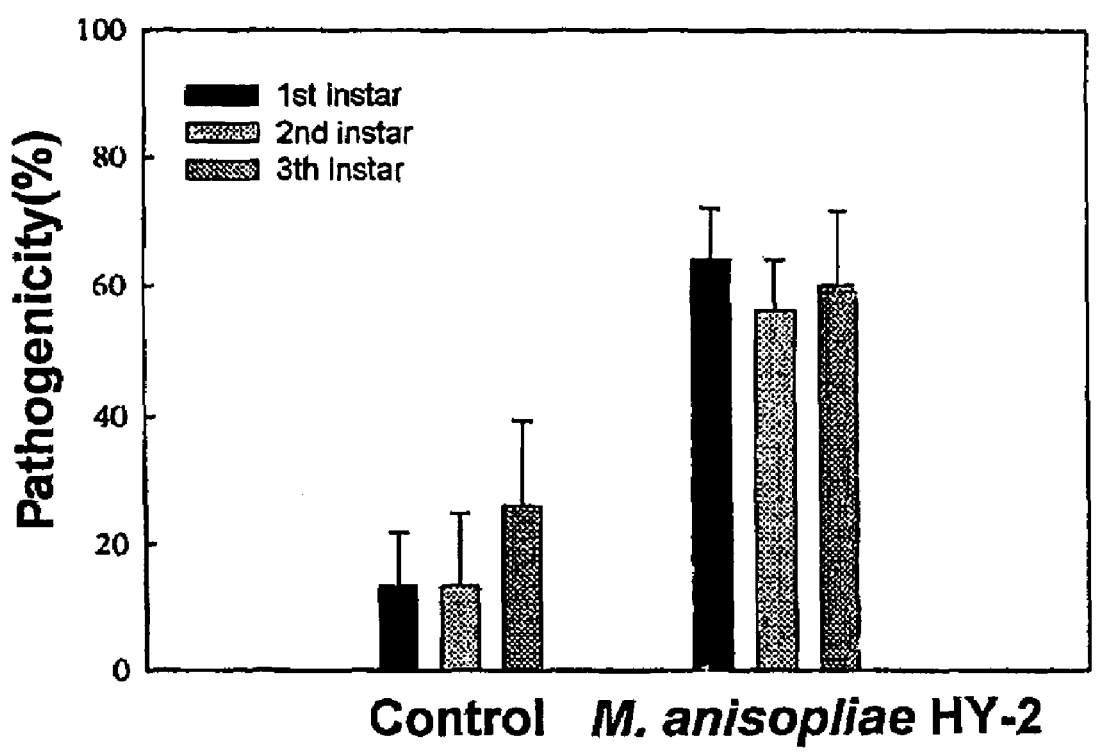
FIG. 5 is a graph showing the insecticidal effect of the *Metarhizium anisopliae* HY-2 of the present invention measured by dipping method.
Figure 6:
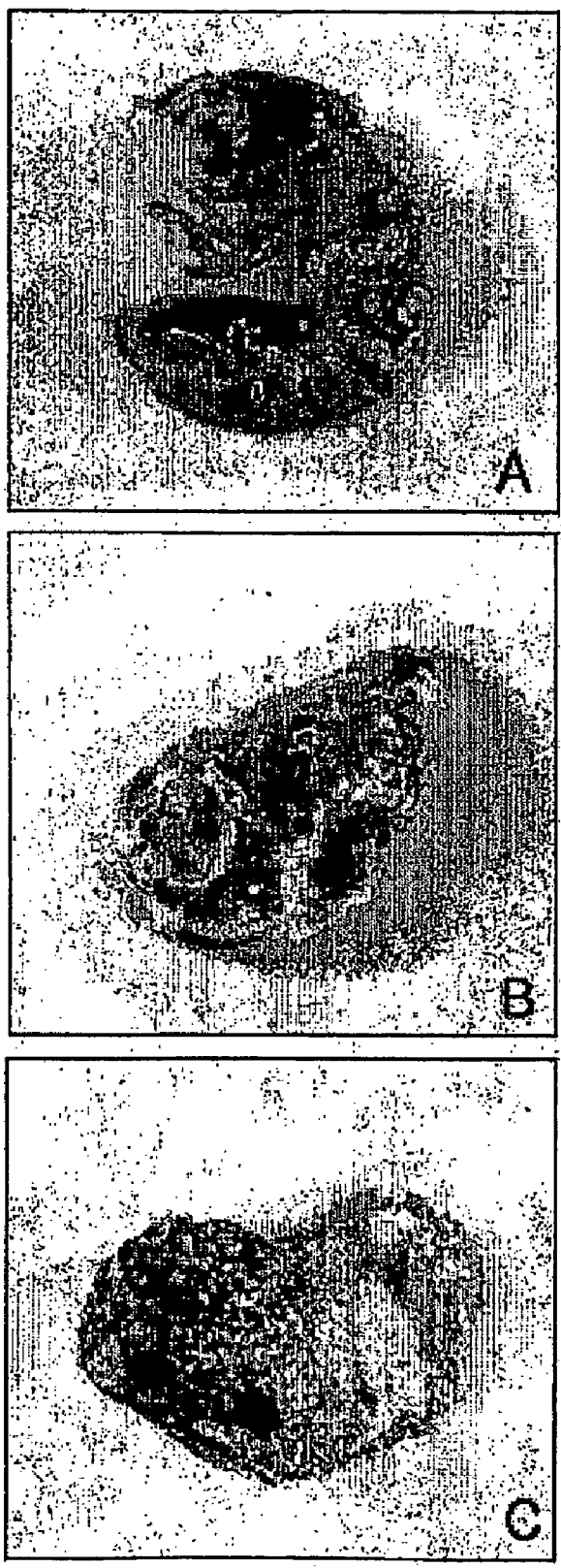
FIG. 6 is a set of photographs showing the larva of an *Adoretus tenuimaculatus* killed by the infection with the *Metarhizium anisopliae* HY-2 of the present invention, A: a photograph of the larva just infected by *Metarhizium anisopliae* HY-2, B: a photograph of the larva three days after being infected by *Metarhizium anisopliae* HY-2, C: a photograph of the larva seven days after being infected by *Metarhizium anisopliae* HY-2

As a result, spore suspension of *Metarhizium anisopliae* HY-2 showed excellent insecticidal effect (56-64%) while a control group showed just 13-26% insecticidal effect (FIG. 5). In addition, more larvae of *Adoretus tenuinaculatus* were confirmed to be infected with *Metarhizium anisopliae* HY-2 as time went (FIG. 6).

Experimental Example 3

Confirmation of Insecticidal Effect by the Contact Toxicity Test

The present inventors confirmed the insecticidal effect of *Metarhizium anisopliae* HY-2 of the present invention on gold bugs by contact toxicity test. Particularly, shaking cultured *Metarhizium anisopliae* HY-2 on CDAY medium for 4 days (26° C., 180 rpm). Put 750 g of solid medium (wheat bran:rice bran:water=4:2:3) into a polypropylen bag (50×22×10 cm$^2$) having 2 sheets of filter membranes (7×7 cm$^2$, effective area diameter 3.5 cm) in it for air permeability and then sealed, which was autoclaved at 121° C. for 30 minutes. Inoculated 9-10 ml of the culture fluid on the solid medium prepared above and then cultured thereof in a culture room for 3-4 weeks in which temperature was maintained at 27° C., the radiation intensity was kept 40 W×2×1.5 and the relative humidity was kept 40-70%. Measured the density of spores with hemacytometer. After crushing the solid medium, adjusted the density to 1×10$^8$ spores/ml and then distributed thereof over humidified artificial feeds (sawdust:bed soil:water=5:3:2). Transferred 10 larvae each from 1$^{st}$ instar, 2$^{nd}$ instar and 3$^{rd}$ instar of Adoretus tenuinaculatus into the above artificial feeds and raised them at 26-28° C. in dark condition. While keeping required humidity for 15 days, investigated pathogenesis.

At that time, regarded insects on which hyphae of fungus were generated as dead insects and insects grown to next instar as live insects. Counted those numbers and presented them with percentage. All experiments were performed 5 times. Used distilled water containing 0.05% tween-80 for a control group.

Figure 7:
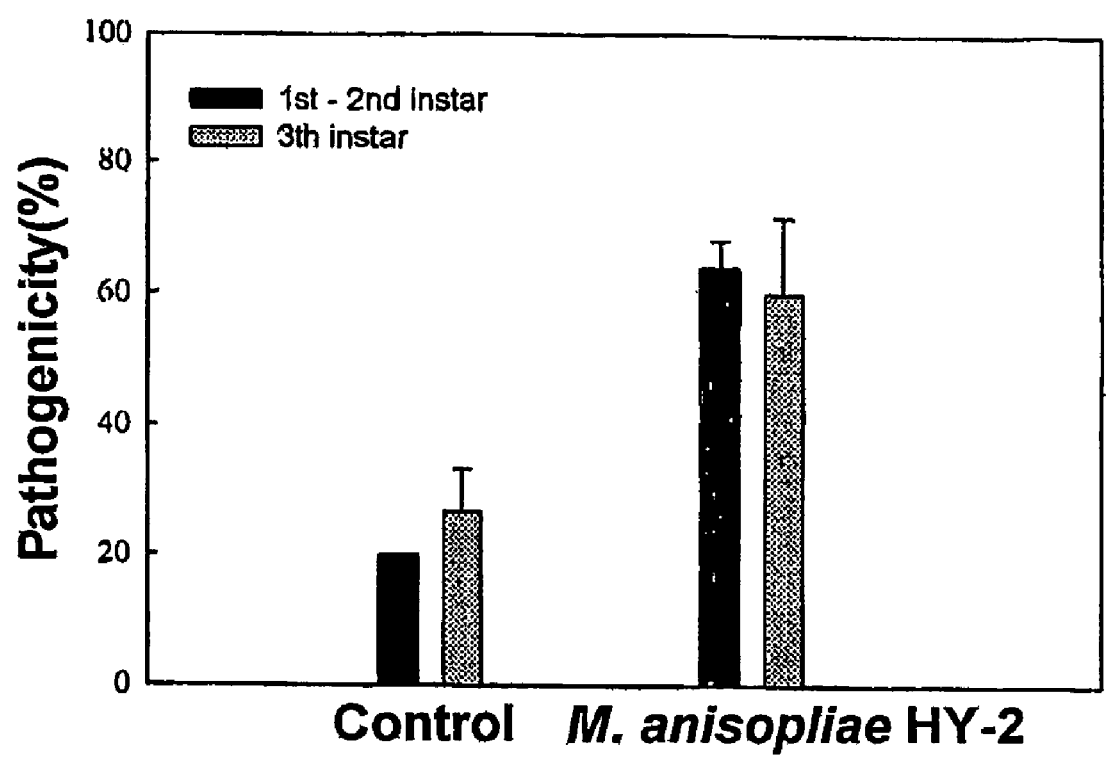
FIG. 7 is a graph showing the insecticidal effect of the *Metarhizium anisopliae* HY-2 of the present invention measured by contact toxicity test.

As a result, *Metarhizium anisopliae* HY-2 of the present invention showed excellent insecticidal effect (60-64%) while a control group showed just 20-27% insecticidal effect (FIG. 7).

INDUSTRIAL APPLICABILITY

As described hereinbefore, the fungus of *Metarhizium* genus has excellent insecticidal effect on larvae of gold bugs, a kind of soil pests harming agricultural crops, so that it can be effectively used for controlling soil pests as an environmental-friendly pesticide.

What is claimed is:

1. An isolated *Metarhizium anisopliae* HY-2 fungus having insecticidal activity to soil pests, deposited with the Gene Bank of the Korea Research Institute of Bioscience and Biotechnology under Accession No: KCTC 0156BP.

2. A microbial insecticide for controlling soil pests containing the fungus of claim 1 as an effective ingredient.

3. The microbial insecticide of claim 2, wherein the microbial insecticide is prepared in the form of wettable powders, granules or capsules.

4. The microbial insecticide of claim 3, wherein the wettable powders are prepared by:
   pulverizing dried solid media inoculated with *Metarhizium anisopliae* HY-2, thereby generating a pulverized powder;
   adding surfactants and diluents to the pulverized powder; and
   pulverizing the pulverized powder.

5. The microbial insecticide of claim 3, wherein the granules are prepared by:
   pulverizing dried solid media inoculated with *Metarhizium anisopliae* HY-2, thereby generating a pulverized powder;
   adding surfactants, adjuvant and diluents to the pulverized powder;
   kneading the surfactants, adjuvant, diluents and pulverized powder with water, thereby generating a dough;
   granulating the dough; and
   drying the dough.

6. The microbial insecticide of claim 4, wherein the surfactant is polycarboxylate, sodium lignosulfonate, sodium dialkyl sulfosuccinate, sodium alkyl sulfonate, polyoxyethylene alkyl phenyl ether, sodium tripolyphosphate, polyoxyethylene alkyl aryl phosphoric ester, polyoxyethylene alkyl aryl ether, polyoxyethylene alkyl aryl polymer, polyoxyalkylene alkyl phenyl ether, polyoxyethylene nonyl phenyl ether, sodium sulfonate or naphthalene formaldehyde.

7. The microbial insecticide of claim 5, wherein the surfactant is polycarboxylate, sodium lignosulfonate, sodium dialkyl sulfosuccinate, sodium alkyl sulfonate, polyoxyethylene alkyl phenyl ether, sodium tripolyphosphate, polyoxyethylene alkyl aryl phosphoric ester, polyoxyethylene alkyl aryl ether, polyoxyethylene alkyl aryl polymer, polyoxyalkylene alkyl phenyl ether, polyoxyethylene nonyl phenyl ether, sodium sulfonate or naphthalene formaldehyde.

8. The microbial insecticide of claim 3, wherein the granules comprise *Metarhizium anisopliae* HY-2 spores, surfactants, nutrients, and disintegrators.

9. The insecticide as set forth in claim 8, wherein the granules are prepared with the following weight ratios: *Metarhizium anisopliae* HY-2 spores 10-60 weight parts, surfactants 2-16 weight parts, nutrients 5-20 weight parts, and disintegrators 10-30 weight parts.

10. The microbial insecticide of claim 9, wherein the granules additionally contain inactive carriers, preservatives, wetting agents, attractants, encapsulating agents, binders, emulsifiers, dyes, or UV protectors.

11. The microbial insecticide of claim 9, wherein the granules are dissolved or suspended in a buffer or fluid.

* * * * *